United States Patent
Bentley

(10) Patent No.: US 9,439,379 B2
(45) Date of Patent: Sep. 13, 2016

(54) BUGLOSSOIDES 'MALIN'

(71) Applicant: Steven Bentley, Cambridge (GB)

(72) Inventor: Steven Bentley, Cambridge (GB)

(73) Assignee: NIAB Trading Ltd. (GB)

( * ) Notice: Subject to any disclaimer, the term of this patent is extended or adjusted under 35 U.S.C. 154(b) by 94 days.

(21) Appl. No.: 14/620,047

(22) Filed: Feb. 11, 2015

(65) Prior Publication Data

US 2016/0227723 A1    Aug. 11, 2016

(51) Int. Cl.
- *A01H 5/10* (2006.01)
- *A01H 5/02* (2006.01)
- *A01H 1/02* (2006.01)

(52) U.S. Cl.
CPC *A01H 5/10* (2013.01); *A01H 1/02* (2013.01); *A01H 5/02* (2013.01)

(58) Field of Classification Search
None
See application file for complete search history.

(56) References Cited

PUBLICATIONS

Retief and Van Wyk 2002, Bothalia 32: 9-13.*

* cited by examiner

*Primary Examiner* — David H Kruse
(74) *Attorney, Agent, or Firm* — Cassandra Bright

(57) ABSTRACT

A new and distinct *Buglossoides arvensis* plant named 'MALIN' characterized by vigorous plant growth and abundant side shoot development. Plants flower early in May and June and do not require vernalization. Seed germination rate is typically 80%. Seeds of the plant are used in the production of the oil commercially known Ahiflower oil.

5 Claims, 5 Drawing Sheets
(5 of 5 Drawing Sheet(s) Filed in Color)

BUGLOSSOIDES 'MALIN'

FIELD OF THE INVENTION

The present invention relates to a new, distinct and stable hybrid of *Buglossoides arvensis*, hereinafter referred it as 'MALIN'. The present invention relates to seeds which are the *Buglossoides arvensis* 'MALIN', as well as, plants and the plant parts produced by these seeds which have all the morphological and physiological characteristics of the *Buglossoides arvensis* 'MALIN'. The present invention also relates to methods for producing these seeds and plants of the *Buglossoides arvensis* 'MALIN'. Furthermore, the present invention relates to method of producing progeny *Buglossoides* plants by crossing *Buglossoides* 'MALIN', as either the female or seed or male or pollen parent, with another *Buglossoides* plant and selecting progeny.

BACKGROUND OF THE INVENTION

The present invention relates to a new, distinct and stable variety of *Buglossoides arvensis*, and hereinafter referred to by the variety denomination 'MALIN'. The new *Buglossoides* ' MALIN' originated from the process of selection of wild collected seed, which was germinated, observed selected and subsequently self-pollinated. Germination, selection and self-crossing were made as part of a controlled breeding program by the inventor at a research greenhouse and outdoor field facility in Cambridge, England. The new variety was initially selected May 19, 2010. The selected seed line was first multiplied in pots and an outdoor field during the summer of 2010 Cambridge, England.

*Buglossoides* is a member of the Boraginaceae family. *Buglossoides* is a genus consisting of 15 species of annual or perennial herbs, native to Europe and Asia. They grow naturally in habitats ranging from sunny scrub to rocky slopes and woodland areas.

*Buglossoides* has been identified as a potentially interesting commercial crop for seed production, with the seeds useful for oil production. The oil derived from *Buglossoides* trades under the commercial name Ahiflower oil. Research has shown that vegetable oils containing stearidonic acid (SDA) could be a dietary source of n-3 fatty acids that would be more effective in increasing tissue eicosapentaenoic acid (EPA) concentrations than are current alpha linolenic acid (ALA) containing vegetable oils. The use of SDA-containing oils in food manufacture could provide a wide range of dietary alternatives for increasing tissue EPA concentrations. Ahiflower oil is indicated to be a more efficient omega-3 alternative to flax, chia, and other ALA-rich dietary oils.

Seeds of *Buglossoides* have been approved for the above mentioned use by the FDA.

*Buglossoides* can be propagated by vegetative, asexual practices. However, this method is impractical for commercial field purposes.

Methods for cultivation and crossing of *Buglossoides* are not well known. However, it is known some varieties are suitable for Winter production, requiring vernalization, whereas some varieties will not require vernalization and produce seeds during the Summer season from Spring planting.

*Buglossoides arvensis* plants are known to produce seeds prolifically. To produce a commercial crop, it has been necessary to address the issue of variety stability, as well as seed dormancy. The inventor has developed a new variety which can be self-pollinated and reproduced true to try from seed. Plants produced by this method are uniform with respect their morphological and physiological characteristics.

A need exists for a greater variety of *Buglossoides* cultivars for commercial seed production, under a variety of environmental conditions. Additionally, a need exists for additional *Buglossoides arvensis* cultivars that can be easily propagated by seed, with consistent results. The new *Buglossoides* 'MALIN' was developed through a controlled breeding program and exhibits unique, desirable and stable characteristics.

SUMMARY OF THE INVENTION

The present invention provides *Buglossoides* plant selections that can be planted in the Spring and produce seeds during Summer, without vernalization. Additionally, plants of 'MALIN' are typically strong and vigorous, more so than known varieties. Agronomic performance and oil content are consistent and desirable for commercial purposes. These qualities distinguish the new cultivar from typical *Buglossoides arvensis* varieties.

These and other objectives have been achieved in accordance with the present invention which provides 'MALIN' as a new *Buglossoides* cultivar that is a product of a planned breeding program conducted by the inventor Steven Bentley, in Cambridge, England.

SUMMARY OF THE INVENTION

The present invention provides *Buglossoides* plant selections that are vigorous, do not require vernzalition and consistently produce seeds with desirable commercial characteristics. Seeds have a thousand grain weight (TGW) around 6.5 g. Confidential research fields average crop yields were between 800 to 900 kg/ha. However, extrapolation of commercial practices indicate that the potential could be as high as 1.3 t/ha. With further growing experience the expected average crop yield should increase closer to 1.3 t/ha.

These and other objectives have been achieved in accordance with the present invention which provides 'MALIN' as new *Buglossoides* cultivar that is a product of a planned breeding program conducted by the inventor Steven Bentley, in Cambridge England.

The new variety 'MALIN' can be produced by sexual reproduction by to produce a population of progeny plants, each of which has the combination of characteristics as herein disclosed for the new variety 'MALIN'.

2500 seeds which are the variety 'MALIN' deposited at the American Type Culture Collection (ATCC) having deposit Designation PTA-122229.

OBJECTS OF THE INVENTION

The present invention related to seeds which produce *Buglossoides arvensis* 'MALIN'. The present invention also relates to *Buglossoides* plants, and parts thereof, having all the physiological and morphological characteristics of *Buglossoides arvensis* 'MALIN'. The present invention relates to a plant produced from seeds which are *Buglossoides arvensis* 'MALIN'. The present invention also relates to plant parts, such as pollen, seeds or inflorescence produced by *Buglossoides arvensis* 'MALIN'.

The present invention relates to a method of producing seed which are *Buglossoides arvensis* 'MALIN'.

The present invention also relates to a method of producing plants having all the physiological and morphological characteristics of the *Buglossoides arvensis* 'MALIN' comprising the steps of (a) self-pollinating *Buglossoides* 'MALIN' a (b) harvesting seeds produced from said cross; and (c) producing plants from said harvested seeds.

The present invention also relates to producing progeny plants from the cross of *Buglossoides arvensis* 'MALIN', as the female or male parent, with another *Buglossoides* plant, and selecting progeny plants from this cross.

BRIEF DESCRIPTION OF THE PHOTOGRAPHS

The patent or application file contains more than one drawing executed in color. Copies of this patent or patent application publication with color drawings will be provided by the Office upon request and payment of the necessary fees.

The accompanying photographs illustrate the overall appearance of the new *Buglossoides arvensis* 'MALIN' showing the colors as true as is reasonably possible with colored reproductions of this type. Colors in the photograph may differ slightly from the color values cited in the detailed botanical description which accurately describes the color of 'MALIN'.

DETAILED BOTANICAL DESCRIPTION

Figure 1:
FIG. 1 shows a single plant of 'MALIN', grown in a greenhouse during Winter months. Plant is approximately 9 weeks, in a 15 cm pot.
Figure 2:
FIG. 2 illustrates the initial seedling selection of 'MALIN', identified with the label "2" in the photo. Growth of this newly selected seedling was more vigorous than other observed seedlings.
Figure 3:
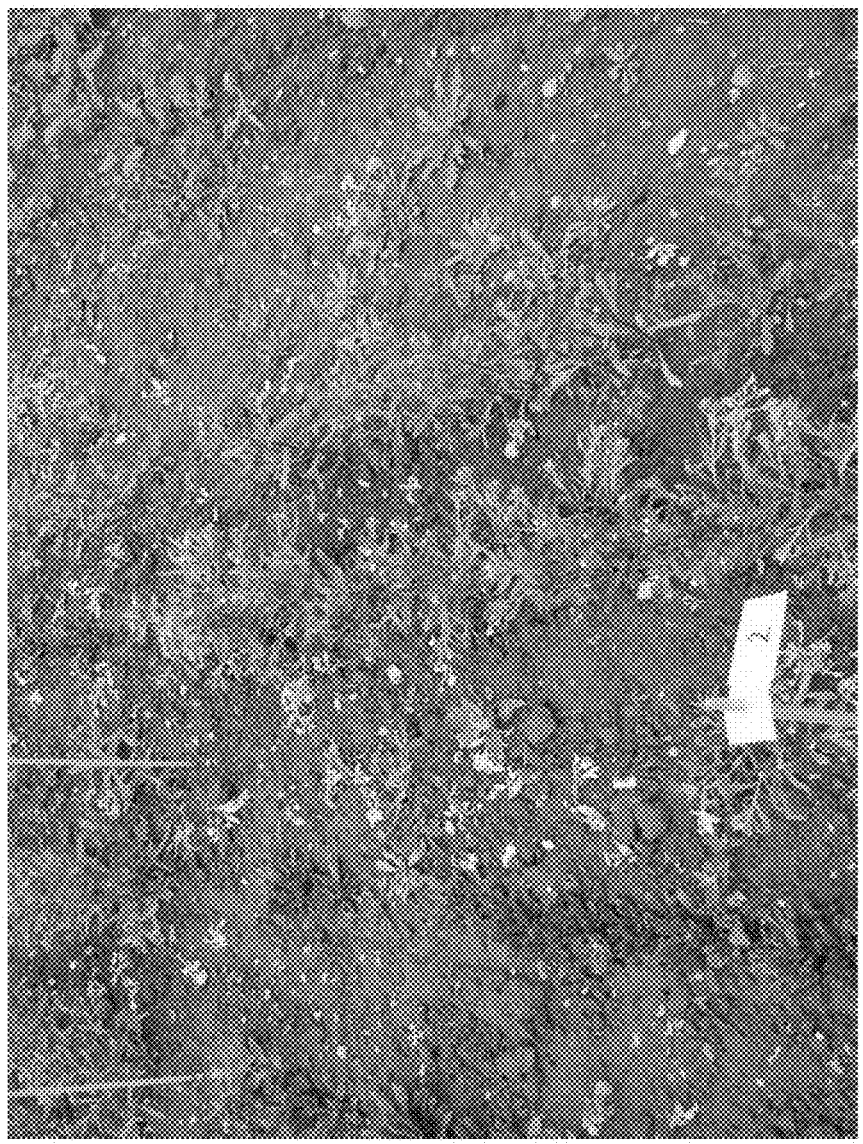
FIG. 3 shows field grown plants of 'MALIN', grown near selections from Kew Gardens. Plants are again identified with the label "2", and more vigorous than surrounding seedlings.
Figure 4:
FIG. 4 illustrates a field crop of 'MALIN', the photo taken May 28, 2014.
Figure 5:
FIG. 5 illustrates the same field crop of 'MALIN', as identified in FIG. 4, this photo taken Jun. 13, 2014. This illustrates the vigorous and rapid growth of the new variety.

The present invention was created by the inventor, Steven Bentley in Cambridge, England.

This invention is directed to a *Buglossoides* plant having all the morphological and physiological characteristics of the variety'MALIN' produced from seeds The new arvensis 'MALIN' can also be produced by asexually reproducing progeny. Asexual reproduction of the new cultivar by vegetative means by cuttings was first performed in 2011, in Cambridge, England. The first 'MALIN' plants propagated through the use of such cuttings are maintained in Cambridge, England and have reproduced at least 5 generations. Subsequent asexual reproduction has demonstrated that the new cultivar reproduces true-to-type and that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be unique characteristics of 'MALIN' which in combination distinguish this *Buglossoides* as a new and distinct cultivar:
1. Vigorous plants
2. Vernalization not required
3. Plants producing many side shoots
4. Earlier flowering than known varieties
5. Improved germination rate, approximately 80%.

Of the few commercial cultivars known to the present inventor, the most similar in comparison to the new *Buglossoides* 'MALIN' is the unnamed, unpatented *Buglossoides arvensis* maintained at Kew Gardens, hereafter referred to as 'Kew Line'. 'MALIN' differ from plants of 'Kew Line in the following:
1. 'MALIN' produces more side shoots per plant
2. 'MALIN' flowers somewhat earlier.
3. 'MALIN' produces approximately 10% dormant seed, whereas this comparator produces approximately 80% dormant seed.

'MALIN' can also be compared to a *Buglossoides arvensis* known to the inventor from Hungary. This variety is also unnamed and unpatented. The inventor refers to this variety as 'Hungary Line'. 'MALIN' differs from this comparator in the following:
1. 'MALIN' does not require vernalization to flower, as required by this comparator.
2. 'MALIN' leaf color is greyed-green, whereas this comparator has green leaves.
3. TGW of 'MALIN' is typically 6.5 g, compared to TGW of 2.6 g of this comparator.

'MALIN' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant.

For example, substantial differences in plant height and diameter; quantity of seeds produced can occur, depending upon environmental conditions.

The aforementioned photographs, together with the following observations, measurements and values describe the new *Buglossoides* 'MALIN' as grown in a greenhouse in Cambridge, England. Plants of 'MALIN' were grown in a greenhouse with temperatures ranging from approximately 20° C. to 25° C. during the day and night temperatures ranging from 10° C. to 15° C. No artificial lighting or photoperiodic treatments were conducted.

Color reference are made to the Royal Horticultural Society Colour Chart (RHS), 2001 edition, except where general colors of ordinary significance are used. Color values were taken under daylight conditions in a greenhouse in Cambridge, England. The age of the plants of 'MALIN' described is about 9 weeks from planting.

Classification;
Botanical: *Buglossoides arvensis* 'MALIN'
Germination: Approximately 3 weeks at 10° C.
Plant:
Growth Habit: Erect. Herbaceous, simple to branching above, multiple stems from taproot, densely antrorse pubescent (hairs appressed).
Pot size of plant described: 20 cm.
Height: To top of foliage: 40 cm
To top of flowers: 40 cm.
Plant Spread: 40 to 50 cm.
Growth Rate: Rapid and vigorous.
Branching Characteristics:
Quantity of Primary Lateral Branches: 4 to 6 on average.

Characteristics of Primary Lateral Branches:
  Diameter: 0.5 to 0.6 cm.
  Length: 35 to 40 cm.
  Color: RHS Greyed-Green group 189B
  Texture: antrorse pubescent
  Strength: Stiff
Internode length: 0.5 to 4 cm
Plant Vigor: Good
  Flowering Season: A fully grown plant can flower year round, starting 16-18 weeks after induction of natural light or through flowering treatment.
  Cold Tolerance: Frost tender. Temperatures below 5° C. may damage plants.
  Fragrance: None
  Foliage:
  Leaf:
  Arrangement: Alternate
  Quantity: Approximately 10 to 15 per branch.
  Average Length: 8 to 10 cm
  Average Width: 1 to 2 cm.
  Shape of blade: linear-oblong to oblanceolate
  Apex: round, obtuse
  Base: tapering, cuneate
  Margin: smooth, entire.
  Texture of top surface: rough
  Texture of bottom surface: rough
  Pubescence: Pilose—standing at an angle.
  Aspect: Foliage tends to be curved—can angle upwards but the more mature leaves are horizontal with the tips curved down.
  Color:
    Young foliage upper side: RHS Greyed-Green group 189A
    Young foliage under side: RHS Greyed-Green group 189C
    Mature foliage upper side: RHS Greyed-Green group 189A
    Mature foliage under side: RHS Greyed-Green group 189D
  Venation:
    Type: pinnate, conspicuous midrib.
    Venation color upper side: RHS Greyed-Green group 189A
    Venation color under side: RHS Greyed-Green group 189C
  Petiole: sessile
  Inforescence:
Natural flowering season: May, June
Days to flowering from seed: Approximately 90 days
Inflorescence and flower type and habit: Monochasial cyme.
Rate of flower opening: 4 to 10 days from bud to fully opened flower.
Flower Longevity on Plant: Average 7 days, longer in cool weather, shorter if warm.
Persistent or Self-Cleaning: Self-Cleaning
Bud:
  Shape: Spherical
  Length: 0.3 cm
  Diameter: 0.2 cm
  Color: RHS White-group 155C
Flower Size:
  Diameter: 0.4 cm.
  Length: 0.5 cm.
Petals:
  Length: 0.2-0.3 cm.
  Diameter: 0.2 cm
  Quantity: 5
  Texture: smooth
  Apex: round, obtuse.
  Color: When opening:
    Upper surface: RHS White-group 155A
    Lower surface: RHS White-group 155B
  Fully Opened:
    Upper surface: RHS White-group 155A
    Lower surface: RHS White-group 155B
  Ageing/Fading:
    Upper surface: RHS White-group 155D
    Lower surface: RHS White-group 155D
Floral Tube:
  Length: 0.3-0.4 cm.
  Diameter: 0.1 cm
  Texture:
    Inner: Pubescent
    Outer: Pubescent
  Color: When Opening:
    Inner surface: From top of tube RHS White group 155A to bottom of tube RHS Greyed-green group 189A
    Outer surface: RHS White group 155A to RHS Greyed-green group 189A
  Fully Opened:
    Inner surface: RHS White group 155A to RHS Greyed-green group 189A
    Outer surface: RHS White group 155A to RHS Greyed-green group 189A
  Ageing/Fading:
    Inner surface: RHS White group 155C to RHS Greyed-green group N189A
    Outer surface: RHS White group 155C to RHS Greyed-green group N189A
Sepals:
  Quantity per flower: 5
  Shape: linear, acuminate
  Length: 0.6-0.7 cm
  Width: 0.1 cm
  Apex: pointed acuminate
  Base: cuneate
  Margin: smooth, entire
  Texture: Pubescent
  Color: RHS Greyed-green group 189A
Peduncle:
  Length: 1 to 2.5 cm
  Color: RHS Greyed green group 191B
  Strength: Strong—becomes woody as seeds ripen
  Angle: straight and almost upright—vertical.
Pedicel:
  Length: 0.1 cm.
  Diameter: 0.1 cm.
  Color: RHS Greyed-green group 189B
Fragrance: none observed
Reproductive Organs:
  Stamens:
  Number: 5
  Filament length: less than 0.1 mm
  Anthers:
    Shape: Dorsifixed, parallel sacks with a groove between
    Length: 0.1 mm
    Color: RHS Greyed yellow 161 (too small to exactly specify under normal light)
  Pollen:
    Color: RHS white group NN155 (too small to specify under normal light)
    Quantity: Abundant
  Pistil:
    Number: 1
    Length: 0.1 cm
    Style:
      Length: between 0.05 and 0.1 cm
      Color: RHS Greyed green (too small to specify under normal light)

Stigma:
    Shape: lobed
    Color: RHS Greyed green (too small to specify under normal light)
SEED/FRUIT: Typical Thousand Grain weight near 6.5 g.
DISEASE/PEST RESISTANCE: Neither resistance nor susceptibility observed.
DISEASE/PEST SUSCEPTIBILITY: Neither resistance nor susceptibility observed.

I claim:

1. A *Buglossoides arvensis* plant named 'MALIN', representative seed deposited at the American Type Culture Collection (ATCC) having deposit Designation PTA-122229.

2. A *Buglossoides arvensis* seed that produces the plant of claim 1.

3. A plant part obtained from the *Buglossoides arvensis* plant of claim 1.

4. A method of producing *Buglossoides arvensis* progeny plant comprising the steps of
    (a) crossing the plant *Buglossoides arvensis* 'MALIN', representative seed having been deposited and having designation PTA-122229, as a female or male parent with another *Buglossoides arvensis* plant, and (b) selecting progeny.

5. The method according to claim 4, wherein the second *Buglossoides arvensis* plant is 'MALIN'.

* * * * *